United States Patent [19]

Kavanagh et al.

[11] 3,978,280

[45] Aug. 31, 1976

[54] IMAGE ANALYSIS APPARATUS

[75] Inventors: Lawrence Grote Kavanagh; Brian Martin Hopkins, both of Huntingdon, England

[73] Assignee: Becton, Dickinson and Company, Rutherford, N.J.

[22] Filed: Apr. 5, 1974

[21] Appl. No.: 458,284

[30] Foreign Application Priority Data

Apr. 6, 1973 United Kingdom............... 16664/73

[52] U.S. Cl.................................. 178/6.8; 178/6; 178/7.5 SE; 178/DIG. 1; 178/DIG. 36
[51] Int. Cl.².......................................... H04N 7/18
[58] Field of Search.................... 178/6.8, 6, DIG. 1, 178/7.5 SE, DIG. 36; 350/8, 19, 20, 37, 40

[56] References Cited
UNITED STATES PATENTS 3,637,997   1/1972   Petersen .......................... 235/92 N
3,801,741   4/1974   Ablett ................................ 178/6.8

*Primary Examiner*—Robert L. Griffin
*Assistant Examiner*—Edward L. Coles
*Attorney, Agent, or Firm*—Irving M. Weiner; Pamela S. Burt

[57] ABSTRACT

Image analysis apparatus has a cathode ray tube and an associated light pen. The light pen can be used to draw on the screen of the cathode ray tube a frame around a feature. A detector connected to receive the video signals only responds to features within that frame. The apparatus can be switched to another mode in which the cathode ray tube displays, to a higher magnification, a point indicated on the screen of the cathode ray tube using the light pen.

8 Claims, 1 Drawing Figure

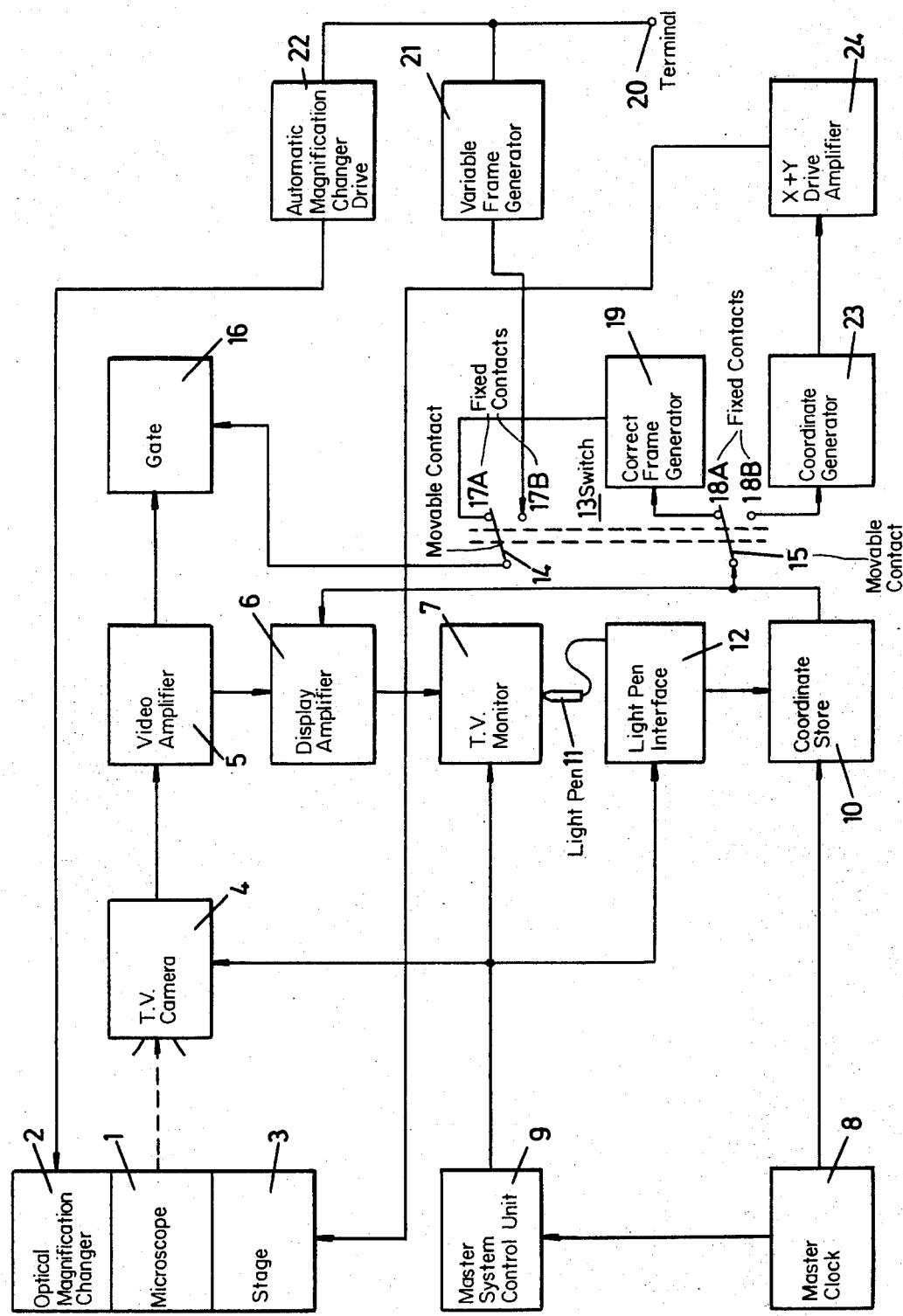

IMAGE ANALYSIS APPARATUS

This invention relates to image analysis apparatus.

It is known to provide apparatus for analysing the display of cathode ray tube. It often occurs that it is desired to analyse a feature appearing in an image on a cathode ray tube and for this purpose it is known to electronically detect the video signals providing that feature on the cathode ray tube. This can be done if the feature illustrated is of a different contrast to the rest of the image in which case a level detector detects the video signals which provide that feature. For this purpose it is possible to provide an adjustable level detector and this method has been called the grey level detection method. By means of this method it is however impossible to isolate a feature which is of interest but which is of the same grey level as other features of the image which are not of interest.

It is an object of this invention to provide image analysis apparatus capable of selecting a feature of interest which is of a similar grey level to other features in the image.

According to this invention there is provided image analysis apparatus comprising a cathode ray tube provided with a light pen, said light pen comprising a photoelectric sensor manually movable over the screen of the cathode ray tube, a store connected to receive signals representative of the horizontal and vertical deflection signals applied to the electron beam of the cathode ray tube, connected to the output of the photoelectric sensor and arranged to store the coordinates of a point on the cathode ray tube where the beam passes over the photoelectric sensor, and gate means connected to the output of the store and to receive video input signals applied to the cathode ray tube and arranged to pass received signals under the control of the coordinates stored in the store.

Preferably the gate means is arranged to enable detection only of signals occurring within a frame defined by the coordinates stored in the store.

In use an operator observes on the cathode ray tube an image and should a particular feature be of interest he encircles it with the photoelectric sensor so as to define a frame which contains only that feature. The video signals producing that feature are then passed through the gate means and can be analysed in any way.

The apparatus may include a television camera coupled to a microscope, the output of the camera being connected to the cathode ray tube and to the gate means.

Suitably the apparatus comprises a magnification changer coupled to the microscope and positioning means for positioning, in relation to the microscope, an object whose image is to be magnified.

Preferably the apparatus includes control means connected to the store, the magnification changer and the positioning means and arranged to cause the field of the microscope to be brought to a position defined by coordinates in the store and to simultaneously increase the magnification of the microscope.

The apparatus according to the invention can provide an image analysis system which has the ability to sequentially analyze various fields of view by moving the object whose image is being analysed. For this purpose it has been suggested to provide a form of programming for the microscope stage by stepping this stage via stepping motors a fixed number of steps each time in both the X and Y directions. However it is often required that the stage movement follows a random pattern to analyze the required fields of interest. In an embodiment of this invention such variable stage movement can be obtained.

Image analysis apparatus in accordance with this invention will now be described, by way of example only, with reference to the accompanying drawing which is a block diagram of the apparatus.

The apparatus has an input optical device which may be a microscope 1 with an automatic optical magnification changer 2 and a stage 3 which can be moved in two directions (these directions are called the X and Y directions) at right angles to each other by the action of two stepping motors (not shown). The object under the microscope 1 is scanned through the microscope 1 by a T.V. camera 4 whose output signal is passed through a video amplifier 5 and a display amplifier 6 to a T.V. monitor 7. The timing sequence for the T.V. camera 4 and T.V. monitor 7 is generated by a master clock 8 and is applied via a master system control unit 9. The master clock 8 also controls a coordinate store 10 which is held in full synchronisation with the T.V. scan.

A light pen 11, comprising a photoelectric sensor is manually movable over the screen of the T.V. monitor 7 and is connected to the store 10 via a light pen interface unit 12. In use, when the spot of the cathode ray tube of the T.V. monitor 7 passes under the photoelectric sensor of the light pen 11 the light pen 11 produces an output signal which is processed by the light pen interface unit 12 and this signal is then fed to the store 10. Since the store 10 is held fully in synchronisation with the T.V. scan signals the position in the store 10 of the signal from the light pen 11 is sufficient to define the position of the light pen 11 in relation to the field of view on the T.V. monitor 7.

The outputs of the store 10 is also connected to the gain control input of the display amplifier 6. A two pole two position switch 13 has two ganged movable contacts 14 and 15 connected respectively to the control terminal of a gate 16 and the output of the store 10 respectively. The movable contacts 14 and 15 are movable from a position (the A position) in which they engage fixed contacts 17A and 18A respectively to a position (the B position) in which they engage fixed contacts 17B and 18B respectively. Fixed contacts 18A and 17A are connected to the input and output respectively of a correct frame generator 19. A terminal 20 which receives a magnification control signal is connected through a variable frame generator 21 to fixed contact 17B and is also connected through an automatic magnification changer drive 22 to changer 2. Fixed contact 18B is connected through an X and Y coordinates generator 23 and X and Y drive amplifier 24 to the stepping motors within the microscope stage 3.

The input of the gate 16 is connected to the output of amplifier 5 and its output is the detected video signal.

The position of the switch 13 selects the mode of use of the light pen 11. With the switch 13 in position A (that shown) the light pen 11 is used to generate a frame for detection by drawing this frame on the T.V. monitor 7.

With the switch 13 in position B the light pen 11 can be used to indicate points on the T.V. monitor 7 relating to points in the field of view which require analysis at a higher magnification.

In use with the switch in position A it is possible for the operator to encircle a feature of interest on the T.V. monitor 7 with the light pen 11 and signals indicative of the coordinates of the indicated points is memorised in the store 10. The information which is placed in the store 10 is fed back to the display amplifier 6 thus enabling the operator to see the points he has drawn on the T.V. monitor 7. When the operator has encircled the feature of interest the correct frame generated 19 will form the store information into a gating signal which is fed to the gate 16. The gate 16 will only pass signals above a certain value and will only pass video information within the generated frame signal when the switch is in position A. Thus information relating only to the encircled feature is obtained and this is the detected video signal.

The mode of the image analysis apparatus as described above is primarily intended for use where standard grey level detection is not sufficient since the wanted feature is of the same grey level as other features in the field of view. This mode of operation is also advantageous where the feature of interest cannot be detected properly owing to its bad definition although it can be clearly seen on the T.V. monitor 7. In this case the operator will again encircle the feature of interest as indicated above but instead of the detector 16 only passing signals above a certain value it passes all video signals within the generated frame signal.

When the switch is in position B the use of the light pen to put signals into the store 10 relating to selected points indicated on the T.V. monitor 7 by the light pen 11 remains unaltered. The difference in the system relates to the use to which the store information is put after it is read from the store. The operation steps are as follows:

An operator places a slide of interest below the microscope at a low magnification (e.g. x1). The system is focussed and the stage 3 manually moved to locate a field of interest. The operator then indicates using the light pen 11 points of interest in the field of view which points are to be analyzed at a higher magnification (these points could be random over the screen or all lie along a path). When the operator has finished denoting these points he indicates the magnification at which he requires the machine to analyze the indicated fields via a control on the machine front panel. The control applies a signal to terminal 20. The apparatus then automatically changes the magnification to that required by means of the signal passed through the drive 22 to the automatic magnification changer 2 and reads the first point from the store 10 to the drive X and Y coordinates generator 21. In this generator 21 true coordinate information for the point read will be generated in the X and Y directions.

This information is fed to the X and Y drive amplifier 24 which in turn will drive the two stepping motors attached to the microscope stage 3 to locate the point in question into the centre of the field of view.

Corresponding to the selected magnification for analysis there is a frame size which will be such as to ensure that only the area indicated initially are analyzed and analyzed only once (i.e. no overlap of information upon successive fields). This frame is obtained by the variable frame generator 21 which receives the signal at terminal 20 and is fed to the detector 16 to gate the detected video signal.

The points are read from the store 10 in succession and each time the associated position on the original field of view is brought to the centre of the field of view at the set higher magnification.

The sequence of reading the information from the store follows the direction of the T.V. raster scan thus it starts in the top left hand corner of the field and finishes in the bottom right.

The drive X and Y coordinates generator 23 is such that it retains coordinate information of the last point read from the store. Thus when a new point is read the difference between the X coordinates and the Y coordinates of the new point and the previous one give the exact movements required and it is these movements which are fed to the X and Y drive amplifiers 24. This reduces the total stage movement required and speeds the operation of the apparatus.

The uses of such an apparatus are many, examples being as follows i. Analysis of a single white cell in a blood sample where there are many in the field of view which will all be of the same grey level.

ii. Analysis of the cytoplasm of a cell which is often such that its boundary runs into the background.

iii. Automatic tracking in the analysis of Histological sections.

We claim:

1. Image analysis apparatus comprising a cathode ray tube; generating means for generating horizontal and vertical deflection signals connected to the cathode ray tube; a light pen comprising a photoelectric sensor manually movable over the screen of the cathode ray tube; a store which is connected to the output of the photoelectric sensor; and gate means which is connected to the output of the store and to receive video signals applied to the cathode ray tube and which passes only those received video signals occurring within a closed path defined by points whose coordinates are stored in the store; a television camera, the output of the camera being connected to the cathode ray tube and to the gate means.

2. An image analysis apparatus according to claim 1, including a microscope coupled to said television camera.

3. Apparatus as claimed in claim 2 which comprises a optical magnification changer coupled to the microscope.

4. Apparatus as claimed in claim 3 which comprises positioning means for positioning, in relation to the microscope, a feature of said closed path whose image is to be magnified.

5. Apparatus as claimed in claim 4 which comprises control means which is connected to the store, the magnification changer and the positioning means.

6. Apparatus as claimed in claim 2 which comprises a magnification changer coupled to the microscope; positioning means for positioning, in relation to the microscope, an object whose image is to be magnified; control means which is connected to the store, the magnification changer and the positioning means; and the control means is connected to the gate means and defines a closed path, the gate means passing only those video signals within that path.

7. Apparatus as claimed in claim 6 wherein the control means is manually controllable to vary the magnification and the size of the defined closed path.

8. Apparatus as claimed in claim 7 which comprises switch means switchable between a position in which it completes a path between the output of the store and the gate means.

* * * * *